(12) United States Patent
Miyoshi et al.

(10) Patent No.: US 7,655,407 B2
(45) Date of Patent: Feb. 2, 2010

(54) METHOD FOR DETECTING TARGET SUBSTANCE UTILIZING PROBE DESORPTION

(75) Inventors: Hayato Miyoshi, Kanagawa (JP); Takeshi Senga, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/029,840

(22) Filed: Feb. 12, 2008

(65) Prior Publication Data

US 2008/0220435 A1    Sep. 11, 2008

(30) Foreign Application Priority Data

Feb. 13, 2007  (JP) .............................. 2007-031557

(51) Int. Cl.
*C12Q 1/68* (2006.01)

(52) U.S. Cl. ......................................................... 435/6

(58) Field of Classification Search ........................ None
See application file for complete search history.

(56) References Cited

U.S. PATENT DOCUMENTS 6,506,564 B1 *  1/2003  Mirkin et al. ................... 435/6
2008/0176263 A1 *  7/2008  Schultz et al. ................ 435/23

OTHER PUBLICATIONS

Jiang et al., "Gold-Labeled Nanoparticle-Based Immunoresonance Scattering Spectral Assay for Trace Apolipoprotein AI and Apolipoprotein B," Clinical Chemistry, 2006, vol. 52, No. 7, pp. 1389-1394.*

Elghanian et al., "Selective Colorimetric Detection of Polynucleotides Based on the Distance-Dependent Optical Properties of Gold Nanoparticles," Science, Aug. 1997, vol. 277, pp. 1078-1081.*

* cited by examiner

*Primary Examiner*—Young J Kim
(74) *Attorney, Agent, or Firm*—Sughrue Mion, PLLC

(57) ABSTRACT

It is an object of the present invention to provide a method for detecting a target substance in a specimen with the use of fine particles, whereby the target substance can be readily detected with the exclusive use of a single type of probe and the detection limit is improved. The present invention provides a method for detecting a target substance in a specimen which comprises the steps of: allowing a complex of a fine particle and a probe to come into contact with a specimen; and detecting changes in physical properties of the fine particle that are caused by desorption of the probe from the fine particle due to interaction between the target substance in the specimen and the probe.

4 Claims, 2 Drawing Sheets

Fe₂O⁻  C₅H₄N₅⁻ (Adenine)

pseudo-target DNA target DNA

METHOD FOR DETECTING TARGET SUBSTANCE UTILIZING PROBE DESORPTION

TECHNICAL FIELD

The present invention relates to a method for detecting a target substance with the use of a complex of a fine particle and a probe, wherein desorption of a probe from a fine particle is utilized.

BACKGROUND ART

Methods for detecting biomarkers (e.g., nucleic acids, proteins, lipids, sugar chains, and hormones) are very important for analytical diagnosis. In particular, detection methods with the use of fine particles have been gaining attention because high reaction efficiency (due to the large specific surface area) and high rates of reaction (due to motility greater than that of a bulk body) are expected to be obtained thereby.

An example of a method for detecting a specimen with the use of a fine particle is described in JP Patent Publication (Kohyo) No. 2004-501340 A. This method is a method for detecting a specimen with the use of a gold nanoparticle to which an oligonucleotide has adhered. The method involves a technique for detecting color changes that appear following aggregation of gold nanoparticles as a result of formation of a crosslinking structure comprising DNA serving as a specimen and an oligonucleotide adhering to a gold nanoparticle. However, according to this method, a crosslinking structure must be formed for detection, and thus at least two different probes are required. In addition, it is necessary to use as many specimens as particles, resulting in insufficiency in terms of the detection limit.

Further, a method for detecting a specimen with the use of an antibody as a probe, wherein formation of a sandwich structure is utilized, (e.g., immunochromatography) has been known. However, when a low-molecular-weight compound such as a hormone is used as a specimen, a sandwich structure is not formed, and thus detection is difficult.

DISCLOSURE OF THE INVENTION

It is an object of the present invention to provide a method for detecting a target substance in a specimen with the use of fine particles, whereby the target substance can be readily detected with the exclusive use of a single type of probe and the detection limit is improved.

As a result of intensive studies in order to achieve the above object, the present inventors have found that aggregation of unstabilized fine particles takes place as a result of desorption of a probe from each fine particle (such probe contributing to dispersion stabilization of fine particles) caused by adding a target substance to be detected to fine particles each having the above probe immobilized thereon by adsorption. In this mechanism, formation of a crosslinking structure or sandwich structure is not necessary for aggregation of fine particles, and thus a target substance can be detected with the exclusive use of a single type of probe. Also, they have found that neighboring fine particles are also involved in aggregation of unstabilized fine particles in such mechanism, contributing to the improvement of the detection limit. The present invention has been completed based on the above findings.

Thus, the present invention provides a method for detecting a target substance in a specimen which comprises the steps of allowing a complex of a fine particle and a probe to come into contact with a specimen; and detecting changes in physical properties of the fine particle that are caused by desorption of the probe from the fine particle due to interaction between the target substance in the specimen and the probe.

Preferably, the probe is a biopolymer.
Also preferably, the probe is a nucleic acid.
Preferably, the nucleic acid is DNA (deoxyribonucleic acid), RNA (ribonucleic acid), PNA (peptide nucleic acid), or LNA (locked nucleic acid).
Preferably, desorption of a probe from a fine particle causes formation of an aggregate of fine particles, resulting in detectable changes in physical properties of a fine particle.
Preferably, detectable changes in physical properties are changes in magnetic responsivity.
Preferably, the fine particle is a magnetic particle.
Preferably, the fine particle is a magnetic nanoparticle having a mean particle size of 1 to 100 nm.

Further, the present invention provides a method for detecting a nucleic acid serving as a detection target which comprises the steps of:

(a) allowing fine particles each having a nucleic acid immobilized thereon to come into contact with a specimen containing a nucleic acid serving as a detection target so as to hybridize the nucleic acid serving as a detection target to the nucleic acid immobilized on a fine particle; and (b) detecting an aggregate of fine particles formed in the above step (a).

Furthermore, the present invention provides a method for detecting an antigenic substance serving as a detection target which comprises the steps of:

(a) allowing fine particles each having an antibody immobilized thereon to come into contact with a sample containing an antigenic substance serving as a detection target so as to cause interaction between the antigenic substance serving as a detection target and the antibody immobilized on a fine particle; and (b) detecting an aggregate of fine particles formed in the above step (a).

According to the method for detecting a target substance in a specimen of the present invention, a target substance can be readily detected with the exclusive use of a single type of probe. In addition, according to the method of the present invention, the detection limit is improved.

BEST MODE FOR CARRYING OUT THE INVENTION

Figure 1:
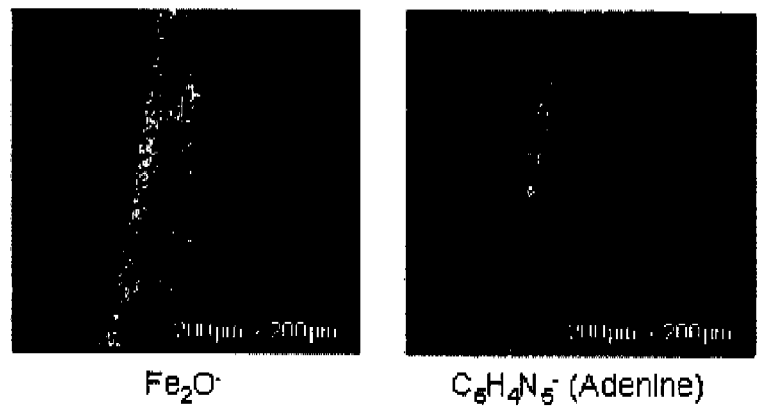
FIG. 1 shows results of surface analysis of DNA-immobilized iron oxide.

Hereafter, embodiments of the present invention are described in detail.

The method for detecting a target substance in a specimen of the present invention comprises the steps of: allowing a complex of a fine particle and a probe to come into contact with the specimen; and detecting changes in physical properties of the fine particle that are caused by desorption of the probe from the fine particle due to interaction between the target substance in the specimen and the probe. According to the present invention, a fine particle having a probe that contributes to dispersion stabilization immobilized thereon by adsorption is used. When a specimen containing a target substance to be detected is allowed to come into contact with fine particles, desorption of a probe from each fine particle, such probe contributing to dispersion stabilization, takes place. Accordingly, fine particles are unstabilized so that they form an aggregate. A target substance in a specimen can be detected by detecting detectable changes derived from an aggregation of fine particles. In addition, desorption of a probe can be detected by a known method for detecting a trace substance. For instance, when a probe is a nucleic acid, desorption of a probe can be detected by PCR using a supernatant.

A fine particle used in the present invention is not particularly limited as long as it can be stably dispersed when forming a complex together with a probe and it experiences changes in physical properties upon desorption of a probe. Any type of such fine particle can be used. For instance, a fine particle that can be used is a fine particle that experiences detectable changes in physical properties when forming an aggregate following desorption of a probe therefrom. Herein, detectable changes in physical properties include changes in magnetic responsivity. With the use of a magnetic particle as a fine particle, changes in magnetic responsivity can be caused as detectable changes in physical properties.

Examples of magnetic particles used in the present invention include salts, oxides, borides, and sulphides of iron, cobalt, or nickel; and rare earth elements having high magnetic susceptibility (e.g., hematite or ferrite). Specific examples of magnetic nanoparticles include magnetite ($Fe_3O_4$). Also, strong magnetic ordered alloys such as FePd, FePt, and CoPt can be used. According to the present invention, a preferred magnetic particle is made of a metallic oxide, for example those which are particularly selected from the group consisting of iron oxide and ferrite (Fe, M)$_3$O$_4$. Herein, iron oxide particularly includes magnetite, maghemite, and mixtures thereof. In the above formula, M represents a metal ion that can form a magnetic metallic oxide when used with the above iron ion. Typical examples thereof are selected from among transition metals, and are most preferably selected from among $Fe^{2+}$, $Zn^{2+}$, $Co^{2+}$, $Mn^{2+}$, $Cu^{2+}$, $Ni^{2+}$, $Mg^{2+}$, and the like. The M/Fe molar ratio is determined based on the stoichiometric composition of a ferrite to be selected. A metallic salt is supplied in a solid or solution form. However, such metallic salt is preferably a chloride salt, bromide salt, or sulfate. Of these, in terms of safety, iron oxide and ferrite are preferable and magnetite ($Fe_3O_4$) is particularly preferable.

The size of a magnetic particle used in the present invention is not particularly limited. Such magnetic particle may be a nanoparticle, microparticle, or milliparticle. However, it is preferably a nanoparticle. The size of a nanoparticle is 1 to 1000 nm. However, a nanoparticle having a mean particle size of 1 to 70 nm is particularly preferable. In addition, in the case of an iron oxide particle, when the particle size exceeds 100 nm, stabilization due to Brownian motion becomes insufficient, and therefore the particle itself shows magnetic responsivity. Thus, when magnetic responsivity is designated as a signal, a particle having the above particle size is preferably used.

According to the present invention, a fine particle is coated with a dispersant, and then a probe can be immobilized by adsorption on such fine particle coated with a dispersant. A dispersant that can be used in the present invention may be a dispersant having a structure that allows it to bind to a fine particle via a coordinate bond or by electrostatic multipoint interaction and having a functional group that can chemically bind to another substance. Examples of a functional group that can chemically bind to another substance include carboxyl group, amino group, hydroxyl group, maleimide group, aldehyde group, ketone group, hydrazide group, and thiol group. Preferably, a carboxyl group or amino group is used. More preferably, a carboxyl group is used.

A method for coating a fine particle with a dispersant as described above is not particularly limited. A method known to a person skilled in the art can be carried out. For instance, during or after formation of particles, the above dispersant is added to a liquid containing the particles, followed by mixing. Thus, the particles can be coated with the above dispersant. In addition, particles may be coated with the aforementioned dispersant by allowing the particles to be dispersed in a solvent (preferably a hydrophilic organic solvent such as methanol, ethanol, isopropyl alcohol, or 2-ethoxyethanol) containing the above dispersant, after washing and purification by a conventional method involving centrifugation, filtration, or the like.

A probe used in the present invention is preferably a substance that contributes to dispersion stabilization of fine particles. As a probe, a biopolymer can be used. For instance, a nucleic acid can be used. Specific examples of a nucleic acid that can be used include DNA (deoxyribonucleic acid), RNA (ribonucleic acid), PNA (peptide nucleic acid), and LNA (locked nucleic acid). In addition, an antibody can be used as a probe.

Immobilization of a probe on a fine particle can be carried out by a method known to a person skilled in the art. For instance, a nucleic acid having an amino group can be immobilized on a fine particle by an amino coupling reaction, such fine particle being coated with a dispersant having a carboxyl group serving as a functional group that can be chemically bound.

According to the present invention, changes in physical properties of a fine particle are detected. Such changes are caused by allowing a complex of a fine particle and a probe to come into contact with a specimen so as to induce desorption of the probe from the fine particle due to interaction between a target substance in the specimen and the probe. For instance, detectable changes in physical properties can be caused as a result of formation of an aggregate of fine particles via desorption of a probe from each fine particle. Meanwhile, when a target substance does not exist in a specimen, interaction with a probe does not take place and thus a fine particle does not experience changes in physical properties. Changes in physical properties of a fine particle include changes in magnetic responsivity, turbidity, and light scattering, and the occurrence or nonoccurrence of sedimentation. Thus, a target substance in a specimen can be detected by detecting such changes. In particular, when a magnetic particle is used as a fine particle, changes in magnetic responsivity can be used as detectable changes in physical properties.

The present invention is hereafter described in greater detail with reference to the following examples, although the technical scope of the present invention is not limited thereto.

EXAMPLES

Example 1

Production of Magnetic Particles

Ferrous acetate (II) (15.66 g) was dissolved in a mixture of ethanol (600 ml) and water (9 ml), followed by heating at 75° C. The obtained solution was mixed with ethanol (300 ml) containing dissolved potassium hydroxide (6.9 g), and further heated at 75° C. for 2 hours. Thereafter, the resulting solution was heated to 100° C. and concentrated at a volume of 300 ml (for approximately 2 hours). After being allowed to stand at 75° C. for 5 hours, the resultant was cooled to room temperature. As a result of the above operation, iron oxide particles dispersed in ethanol were obtained.

Example 2

Coating with a Dispersant

Water (70 ml) was added to ethanol containing dispersed iron oxide particles (30 ml) obtained in Example 1 for precipitation of iron oxide particles. Then, the supernatant was removed therefrom, followed by washing. Subsequently, a compound (dispersant) represented by the following formula (1) was dispersed in water (60 ml):

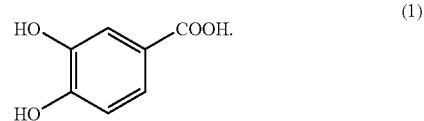

(1)

Then, the obtained solution was added to washed iron oxide particles such that the compound was added at a weight that was 20% of that of iron oxide. Ultrasonication was carried out for an hour, followed by overnight agitation at room temperature. Accordingly, water-dispersible magnetic particles were obtained.

Example 3

Immobilization of Nucleic Acid by Adsorption

The water-dispersible magnetic particles obtained in Example 2, DNA having the sequence represented by SEQ ID NO: 1, and MES buffer were mixed and adjusted to final concentrations of 1 g/L, 50 µM, and 0.1 M, respectively. The resulting mixture was shaken overnight and repeatedly subjected to centrifugation, removal of the supernatant, and redispersion. Thus, unimmobilized DNAs were removed.

(5')-GGGCATGGGTCAGAAGGATT-(3') (SEQ ID NO: 1)

Example 4

Confirmation of Immobilization of Nucleic Acids by Adsorption

The DNA-immobilized iron oxide produced in Example 3 was subjected to surface analysis by TOF-SIMS. A primary ion gun (V and $Bi^{3+}$) was used and an electron gun (20 eV) was used for charge referencing. A sample used was obtained by adding a dispersion solution dropwise to an Si wafer that had been washed with nitric acid, pure water, MeOH, and acetone in such order, followed by vacuum drying.

As shown in FIG. 1, the region containing an iron-oxide-derived fragment corresponded to the region containing a DNA-derived fragment. Thus, DNA was confirmed to be adsorbed to iron oxide particles.

Example 5

Evaluation of the Amount of Immobilized Nucleic Acid

In order to confirm immobilization of nucleic acid, nucleic acid to which a fluorescent dye (Cy5) had been bound was immobilized by the technique described in Example 3.

After unimmobilized nucleic acid was removed by centrifugation, nucleic-acid-immobilized water-dispersible magnetic particles were redispersed, and then fluorescence (excitation: 640 nm, detection: 680 nm) was measured. Consequently, nucleic acid was immobilized at molar ratio of 0.01% to iron oxide. As a result of measurement by light scattering, it was found that water-dispersible magnetic particles used in the examples formed an aggregate of approximately 50 nm. Herein, 50-nm particles comprised $10^5$ to $10^6$ $Fe_3O_4$ units, indicating that 10 to $10^2$ nucleic acid molecules were immobilized on a single particle.

In addition, the nucleic acid used is described below in detail.

(5')-GGGCATGGGTCAGAAGGATT-(3')-Cy5 (SEQ ID NO: 1)

Example 6

Preparation of Target DNA and Pseudo-Target DNA

With the use of the following primers, target DNA and pseudo-target DNA were obtained by PCR. In addition, PCR was carried out with the solution composition shown in Table 1 and the temperature profile shown in Table 2. Plasmid DNA of human β-actin was used as a template.

(5')-GGGCATGGGTCAGAAGGATT-(3') (SEQ ID NO: 2)

(5')-CATGTCGTCCCAGTTGGTGA-(3') (SEQ ID NO: 3)

(5')-CCGAGCGGGAAATCGTGCGT-(3') (SEQ ID NO: 4)

(5')-TCGTAGCTCTTCTCCAGGGA-(3') (SEQ ID NO: 5)

TABLE 1

| PCR solution composition | |
| --- | --- |
| Tris-HCl | 2 mM |
| KCl | 10 mM |
| EDTA | 0.01 mM |
| DTT | 0.1 mM |
| Tween 20 | 0.05% |
| Nonidet P-40 | 0.05% |
| Glycerol | 5% |
| dNTP | 0.25 mM (each) |

TABLE 2

| PCR temperature profile | | |
| --- | --- | --- |
| 94° C. | 5 min | |
| ↓ | | |
| 94° C. | 20 sec | |
| 60° C. | 30 sec | ×25 |
| 72° C. | 90 sec | |
| ↓ | | |

Figure 2:
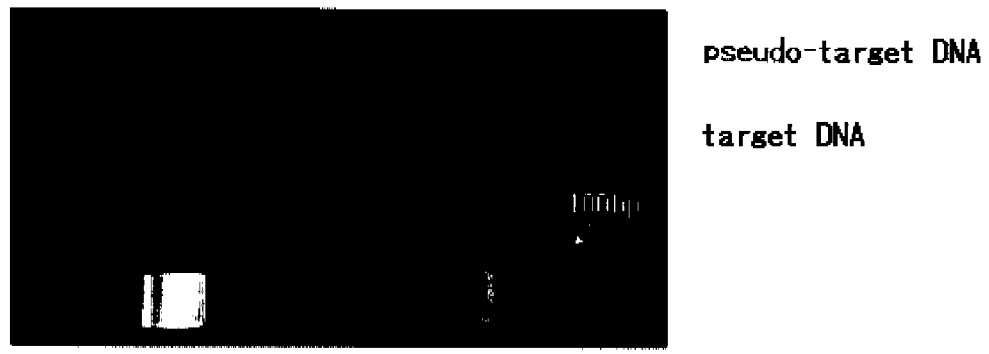
FIG. 2 shows results of electrophoresis of target DNA and pseudo-target DNA.

It was confirmed that PCR of target DNA and PCR of pseudo-target DNA were successfully carried out by electrophoresis (FIG. 2). Thereafter, target DNA and pseudo-target DNA were purified by generally used ethanol precipitation and then preserved.

Example 7

Target DNA Detection Experimentation

NaCl was added to a final concentration of 0.1 M to the nucleic-acid-immobilized water-dispersible magnetic particles obtained in Example 3. Then, the target aqueous solution and the pseudo-target (DNA having a different sequence) aqueous solution prepared in Example 6 and water were separately added thereto (10 μl each).

Figure 3:
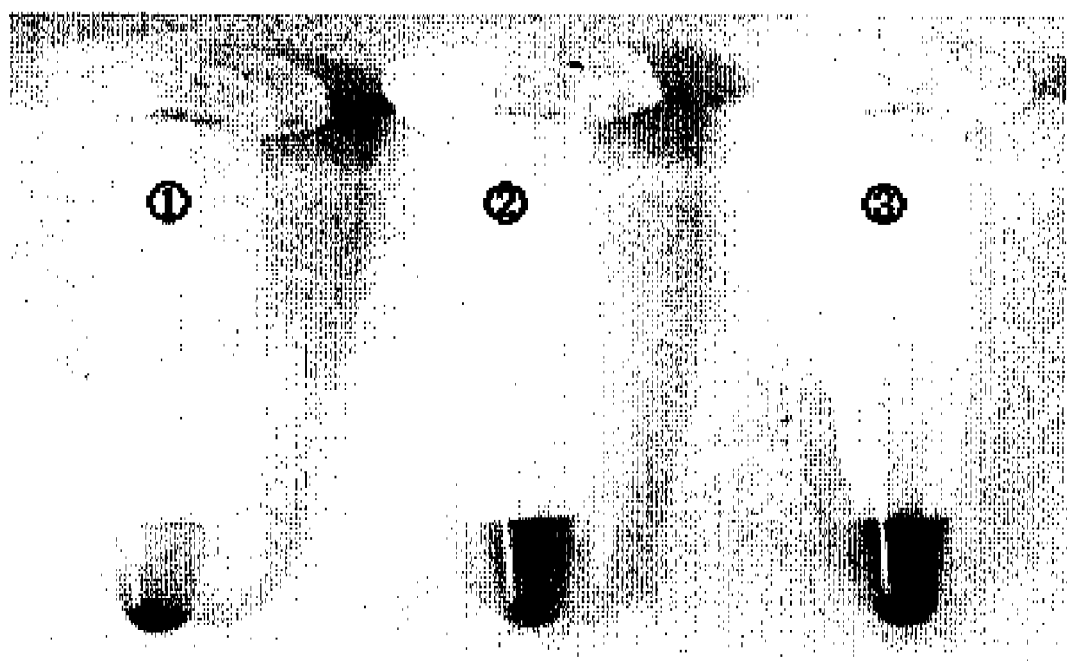
FIG. 3 shows results of target DNA detection experimentation. The figure shows results of the addition of a target aqueous solution (1), the addition of a pseudo-target aqueous solution (2), and the addition of the equal volume of water (3).

The resulting solution was heated at 96° C. for 1 minute and then allowed to stand at 60° C. for 5 minutes. Subsequently, a magnet was placed closed to the solution for 30 seconds and sedimentation conditions were observed. FIG. 3 shows the observation results. In the system containing target DNA, water-dispersible magnetic particles showed magnetic responsivity. Meanwhile, in the system containing water or a pseudo-target, the particles did not show magnetic responsivity. The above results indicate that sequence specific detection of DNA can be carried out with the use of water-dispersible magnetic particles obtained in the present invention.

In addition, the detection limit was evaluated. When a specimen was added to a final concentration of 1 μM, magnetic particles showed magnetic responsivity, and thus detection was possible. The above detection limit was superior to the results (60 μM) described in "SCIENCE, Vol. 277, 1078-1081 (1997)."

The invention claimed is:

1. A method for detecting a target substance in a specimen which comprises the steps of: allowing a complex of a fine particle and a probe to come into contact with a specimen; and detecting changes in physical properties of the fine particle that are caused by desorption of the probe from the fine particle due to interaction between the target substance in the specimen and the probe, wherein the fine particle is a magnetic nanoparticle having a mean particle size of 1 to 100 nm,
   wherein desorption of a probe from a fine particle causes formation of an aggregate of fine particles, resulting in detectable changes in physical properties of a fine particle, and
   wherein said detectable changes in physical properties are changes in magnetic responsivity.

2. The method of claim 1 wherein the probe is a biopolymer.

3. The method of claim 1 wherein the probe is a nucleic acid.

4. The method of claim 3 wherein the nucleic acid is DNA (deoxyribonucleic acid), RNA (ribonucleic acid), PNA (peptide nucleic acid), or LNA (locked nucleic acid).

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 1
gggcatgggt cagaaggatt                                                  20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 2
gggcatgggt cagaaggatt                                                  20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 3
catgtcgtcc cagttggtga                                                  20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 4
ccgagcggga aatcgtgcgt                                                  20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 5
tcgtagctct tctccaggga                                                  20
```